Jan. 13, 1959 E. S. BOERNER Plant Pat. 1,797
ROSE PLANT
Filed June 3, 1958
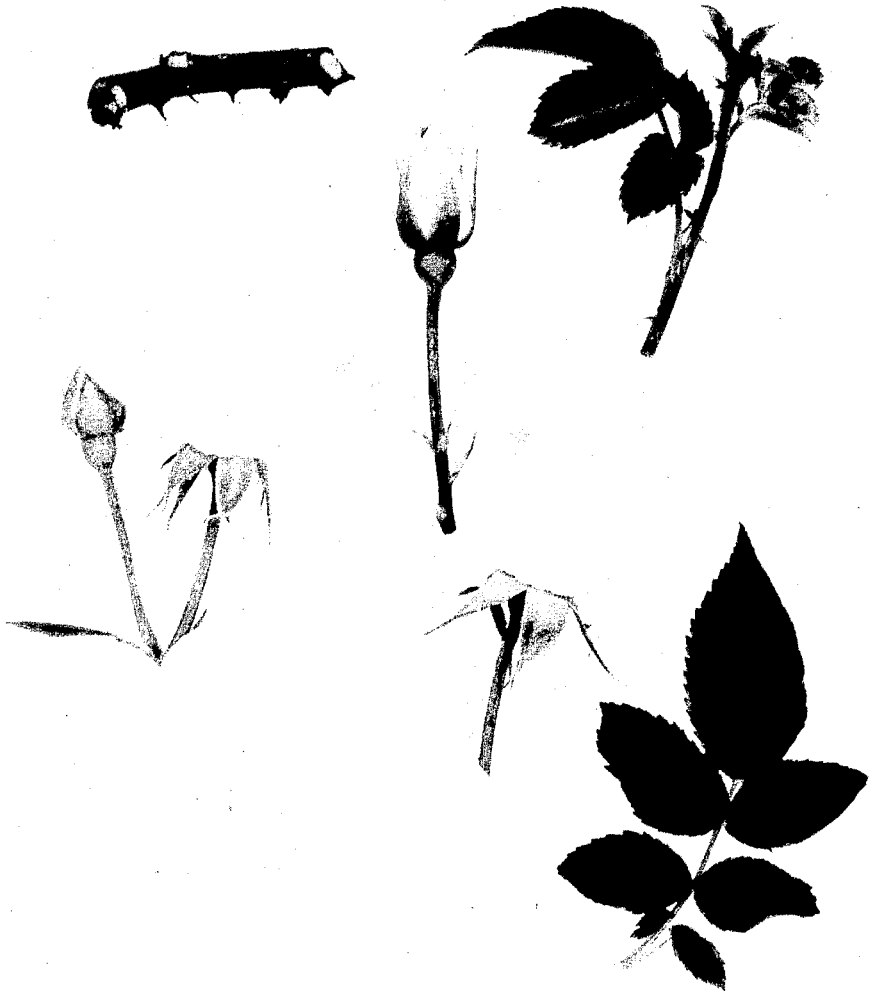
Inventor.
E. S. Boerner
By: Robb & Robb
Attorneys United States Patent Office Plant Pat. 1,797
Patented Jan. 13, 1959

1,797

ROSE PLANT

Eugene S. Boerner, Newark, N. Y., assignor to Jackson & Perkins Company, Newark, N. Y., a corporation of New York Application June 3, 1958, Serial No. 739,640

1 Claim. (Cl. 47—61)

The present invention relates to a new and distinct variety of rose plant of the large-flowered polyantha class, which was originated by me by crossing an unnamed and unpatented highly colored floribunda seedling derived from "Pinocchio" (Plant Patent No. 484) × "Climbing Mrs. Sam McGredy" (Plant Patent No. 394) and another unnamed and unpatented seedling of the same parentage, with the variety "Fashion" (Plant Patent No. 789).

The primary objective of this breeding was to produce a new rose variety having the hardiness and flower color of the variety "Fashion," combined with the good qualities of the highly colored unnamed floribunda seedling referred to above. This objective was fully achieved, along with other desirable improvements, as evidenced by the following unique combination of characteristics which are outstanding in the new variety and distinguish it from its parents, as well as from all other varieties of which I am aware:

(1) Dark Cress Green foliage which contrasts strikingly with the flower color;

(2) Cup-shaped flowers and individual florets of large size;

(3) Long-lasting flower qualities suitable for both indoor and outdoor use;

(4) Good hardiness; and (5) A distinctive La France Pink general color tonality of the flowers, lightly overcast with Eosine Pink.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed descripiton of my new variety, with color terminology in accordance with Ridgway's Color Standards and Nomenclature:

Parentage: Seedling.

*Seed parent.*—An unnamed seedling derived from ("Pinocchio" × "Climbing Mrs. Sam McGredy") × ("Pinocchio" × "Climbing Mrs. Sam McGredy").

*Pollen parent.*—"Fashion."

Classification:

*Botanic.*—Large-flowered Polyantha.

*Commercial.*—Floribunda.

*Flower*

(Observations made from specimens grown in a greenhouse at Newark, New York, in the early morning and in the latter part of February.)

Blooming habit: Recurrent—Continuous.

Bud:

*Size.*—Medium.

*Form.*—Ovoid; is not affected by wet or hot weather.

*Color.*—When sepals first divide—Eugenia Red, Plate 13. When petals begin to unfurl—Alizarine Pink, Plate 13, lightly overcast with Venetian Pink, Plate 13. When half-blown: inside of petals—Light Jasper Red, Plate 13; reverse of petals—Thulite Pink, Plate 26, lightly overcast with Cameo Pink, Plate 26.

*Sepals.*—Slightly branched; curl back when petals begin to unfurl. Color: inside—Yellowish Glaucous, Plate 41; outside—Light Elm Green, Plate 17.

*Calyx.*—Color—Light Elm Green, Plate 17. Shape—Funnel. Size—small. Aspect—smooth. Odor when rubbed—none.

*Peduncle.* — Length — short. Aspect — smooth. Strength—bending; slender. Color—Light Bice Green, Plate 17.

*Opening.*—Opens up well; is not affected by adverse weather conditions.

Bloom:

*Size.*—Medium. Average size when fully expanded—from 2¼ inches to 3¼ inches.

*Borne.*—Several together and in pyramidal clusters.

*Stems.*—Medium length; strong.

*Form (when first open).*—Cupped. Permanence—flattens.

*Petalage.*—Double (full but open center). Number of petals under normal conditions—from 40 to 45.

*Color.*—Center of flower—Geranium Pink, Plate 1, lightly overcast with La France Pink, Plate 1. Outer petals—Hermosa Pink, Plate 1. Base of petals (aiglet)—Pale Lumiere Green, Plate 27. Inside of petals—La France Pink, Plate 1, lightly overcast with Eosine Pink, Plate 1. Reverse of petals—Cameo Pink, Plate 12. General tonality from a distance—La France Pink, Plate 1, lightly overcast with Eosine Pink, Plate 1.

*Discoloration.*—General tonality at end of first day—La France Pink, Plate 1, lightly overcast with Eosine Pink, Plate 1. Second day—La France Pink, Plate 1, lightly overcast with Eosine Pink, Plate 1. Third day—La France Pink, Plate 1, lightly overcast with Eosine Pink, Plate 1.

Petals:

*Texture.*—Thick; is not affected by wet or hot weather.

*Appearance.*—Inside—satiny. Outside—shiny.

*Form.*—Oval; slightly notched.

*Arrangement.*—Imbricated (regularly arranged shingle-like).

*Petaloids in center.*—Few; small.

*Persistence.*—Drop off cleanly.

*Fragrance.* — Moderate. Nature — fruity (russet apple).

*Lasting quality.*—On the plant—very long. As cut flower—very long.

*Genital organs*

Stamens, anthers: Small; few; regularly arranged around styles. Color—Zinc Orange, Plate 15.

Stamens, filaments (threads): Medium length. Color—Marguerite Yellow, Plate 30.

Pollen: Color—Cartridge Buff, Plate 30.

Styles: Loosely separated; uneven length; short; thin.

Stigmas: Color—Ivory Yellow, Plate 30.

Ovaries: All enclosed in calyx.

Hips: None.

Seeds: None

*Plant*

Form: Bush.

Growth: Vigorous; upright.

Foliage: Compound of 5 to 7 leaflets.

*Size.*—Medium.

*Quantity.*—Normal.

*Color.*—New foliage: upper side—Chromium Green, Plate 32, with serrations Mineral Red, Plate 27; under side—Victoria Lake, Plate 1. Old foliage: upper side—Dark Cress Green, Plate 31; under side—Light Cress Green, Plate 31.

*Shape.*—Oval pointed.

*Texture.*—Upper side—leathery. Under side—smooth.

*Ribs and veins.*—Ordinary.

*Edge.*—Serrated (saw-toothed).

*Serration.*—Both double and single; small.

*Leaf stem.*—Color—Light Hellebore Green, Plate 17. Under side—prickly.

*Stipules.*—Short; smooth.

Wood:

*New wood.*—Color—Deep Dull Yellow-Green, Plate 1. Bark——smooth.

*Old wood.*—Color—Forest Green, Plate 17. Bark—smooth.

Thorns:

*Thorns.*—Quantity: on main stalks from base—many; on laterals from stalk—many. Form—narrow base; medium length; straight. Color (when young)—Indian Lake, Plate 26. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the unique combination of Dark Cress Green foliage which contrasts strikingly with the flower color, cup-shaped flowers and large individual florets, long-lasting flower qualities suitable for both indoor and outdoor use, good hardiness, and a distinctive La France Pink general color tonality of the flowers, lightly overcast with Esosine Pink.

No references cited.